United States Patent [19]

Hodel

[11] 4,103,014
[45] Jul. 25, 1978

[54] USE OF 4aRS,5SR,9bRS-2-ETHYL-1,3,4,4a,5,9b-HEXAHYDRO-7-METHYL-5-p-TOLYL-2H-INDENO[1,2-C]PYRIDINES IN INHIBITING SPERMATOGENESIS

[75] Inventor: Christian Hodel, Basel, Switzerland

[73] Assignee: Sandoz Ltd., Basel, Switzerland

[21] Appl. No.: 817,418

[22] Filed: Jul. 18, 1977

[30] Foreign Application Priority Data

Jul. 16, 1976 [GB] United Kingdom ............... 29691/76

[51] Int. Cl.² .......................................... A61K 31/445
[52] U.S. Cl. ................................................... 424/267
[58] Field of Search ........................................ 424/267

[56] References Cited
PUBLICATIONS

Enoether et al.–Chem. Abst. vol. 74 (1971) p. 22707r.

Primary Examiner—Sam Rosen
Attorney, Agent, or Firm—Gerald D. Sharkin; Robert S. Honor; Timothy G. Rothwell

[57] ABSTRACT

The present invention relates to the use of the known compound of formula

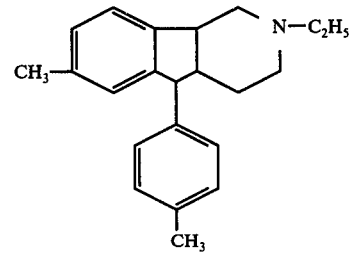

for an agent for inhibiting spermatogenesis in male animals.

6 Claims, No Drawings

USE OF 4aRS,5SR,9bRS-2-ETHYL-1,3,4,4a,5,9b-HEXAHYDRO-7-METHYL-5-p-TOLYL-2H-INDENO[1,2-C]PYRIDINES IN INHIBITING SPERMATOGENESIS

The present invention relates to the (4aRS,5SR,9bRS) compound of formula I,

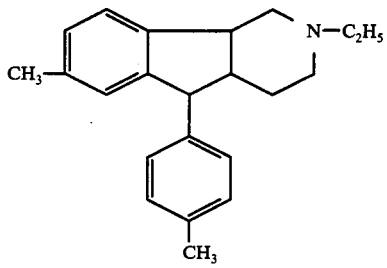

which is 4aRS,5SR,9bRS-2-ethyl-1,3,4,4a,5,9b-hexahydro-7-methyl-5-p-tolyl-2H-indeno[1,2-C]pyridine.

The compound is disclosed in U.S. Pat. No. 3,678,507.

It has now been found that the compound of formula I is useful as an agent for inhibiting spermatogenesis in male animals, e.g. mammals, as indicated by an arrest of spermatogenesis in the following tests:

Test one

The compound is administered s.c. in an oil suspension of 0.2 ml in volume to rats (Ivanovas-Wister strain — 8 weeks old). The amount of compound administered is 30 mg/kg/day over three weeks. A single dose is given on Monday to Thursday. On Friday a double dose is given. The compounds lead to a drastic reduction of the weight of the testes and sperm concentration in the Cauda epididymis in sacrificed animals, as determined in conventional manner (see Experimental and Molecular Pathology 23, 1975 Supplement No. 2). Histology reveals a severe impairment of spermatogenesis.

The above experiment was repeated by p.o. administration of an aqueous solution of the compound to OFA Sandoz rats. Again, a drastic reduction of the weight of the testes and sperm concentration in the Cauda epididymis and a severe impairment of spermatogenesis were observed.

In both experiments, the observed effects diminished following cessation of the treatment and the rats reverted to their normal state after approximately ten weeks.

Test two

The compound is administered enterally at a dose of from 10 to 30 mg/kg/day to young and adult male beagles for up to 4 weeks. A reduction in the weight of the testes obtained after sacrifice of the animals is observed. Histology alternatively reveals a severe impairment of spermatogenesis. No more spermatozoa could be detected in the ejaculate. Following cessation of the treatment, the dogs reverted to their normal state after approximately thirteen weeks.

The compound is therefore useful in inducing permanent or temporary sterility in male animals.

For the above mentioned use the dosage will, of course, vary depending on the mode of administration and therapy desired. However, in general, satisfactory results are obtained when administered at a daily dosage of from about 0.1 mg to about 50 mg per kg of animal body weight, preferably from about 1 mg to about 50 mg per kg of animal body weight, conveniently given in divided doses 2 to 4 times a day or in sustained release form. For the larger mammal, the total daily dosage is in the range from about 10 to about 1000 mg, preferably from about 100 to about 1000 mg, and dosage forms suitable for oral administration comprise from about 2 mg to about 500 mg, preferably from about 25 mg to about 500 mg of the compounds admixed with a solid or liquid pharmaceutical carrier or diluent.

The compound of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methanesulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastro-intestinal tract and thereby provide sustained action over a long period.

The preferred compositions from the standpoint of ease of administration are solid compositions, particularly solid-filled gelatin capsules and tablets.

However, it is also preferred to use a depot formulation, particularly one suitable for s.c. or i.m. administration.

Another aspect of the invention relates to the use of the compound of formula I as a chemical sterilant for the control of pest populations, particularly for aves and rodents. These compounds can be prepared as a pre-mix concentrate containing 1 to 70 wt/% active component in a suitable carrier which can then be blended into foodstuffs or liquids to form bait formulations for the indicated pest. Suitable carriers include flavored or unflavored solid carriers which may be water soluble, e.g. sugars such as sucrose, glucose and the like, or water insoluble such as starch, dicalcium phosphate and the like. Active components which are liquids at normal conditions may be absorbed into suitable porous supports such as calcium silicate, silicic acid, silicon dioxide, calcium carbonate, etc. Hydrophobic forms of the active component, i.e. the free base, may be dissolved in edible vegetable oils. Protected forms of the active component concentrates can be prepared by emulsifying or dispersing such component into a solution of gum of acacia and then spray drying.

The aforesaid concentrates may be employed in preparing suitable bait formulations by blending with liquids, i.e. drinking water which can be flavored with a sugar such as sucrose, or into solid foodstuffs. Suitable foodstuffs useful as bait materials include cereal grain or mixtures such as rat chow or oatmeal which can optionally contain glycerine, animal renderings; fish meal and the like. It is desirable to utilize the compound in a concentration of from about 0.05 to 1 wt/% based on the final bait composition, most preferably in the range of from about 0.1 to 0.5 wt/%. Selection of a particular composition will, of course, depend on the species of pest involved and the average intake of the baited food by the pest in the wild at a single feeding.

In one example the compound (4aRS,5SR,9bRS)-2-ethyl-1,3,4,4a,5,9b-hexahydro-7-methyl-5-p-tolyl-2H-indeno[1,2-c]pyridine hydrochloride is effective in inhibiting spermatogenesis in a larger mammal when administered p.o. at a dosage of from about 10 to about 1000 mg a day.

What is claimed is:

1. A method of inhibiting spermatogenesis in male animals, which comprises administering to a male animal in need of such treatment a therapeutically effective amount of a compound of the formula

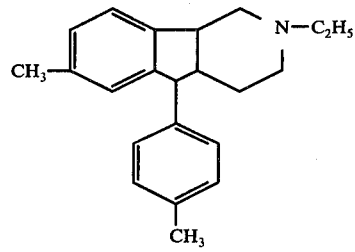

or a pharmaceutically acceptable acid addition salt form thereof.

2. The method of claim 1, in which the compound is 4aRS,5SR,9bRS-2-ethyl-1,3,4,4a,5,9b-hexahydro-7-methyl-5-p-tolyl-2H-indeno[1,2-c]pyridine hydrochloride.

3. The method of claim 1 wherein the compound is administered orally at a daily dosage of from about 10 milligrams to about 1000 milligrams.

4. The method of claim 1 wherein the compound is administered orally at a daily dosage of from about 100 milligrams to about 1000 milligrams.

5. The method of claim 1 wherein the compound is orally administered in a unit dosage form comprising from about 2 milligrams to about 500 milligrams per unit dosage.

6. The method of claim 1 wherein the compound is orally administered in a unit dosage form comprising from about 25 milligrams to about 500 milligrams per unit dosage.

* * * * *